[12] United States Patent
Aceti et al.

(10) Patent No.: US 11,266,531 B2
(45) Date of Patent: Mar. 8, 2022

(54) DEVICE FOR PROTECTING THE HUMAN SENSORY HEARING SYSTEM WHILE RETAINING QUALITY SOUND

(71) Applicant: EAROS, Inc., New York, NY (US)

(72) Inventors: John G. Aceti, New Hope, PA (US); Wayne J. Staab, Dammeron Valley, UT (US); Peter T. Ragonetti, Brooklyn, NY (US); Ron Andre Madramotoo, New York, NY (US)

(73) Assignee: EAROS, INC., New York, NY (US)

( * ) Notice: Subject to any disclaimer, the term of this patent is extended or adjusted under 35 U.S.C. 154(b) by 944 days.

(21) Appl. No.: 15/282,371

(22) Filed: Sep. 30, 2016

(65) Prior Publication Data

US 2017/0095372 A1 Apr. 6, 2017

Related U.S. Application Data

(60) Provisional application No. 62/284,496, filed on Oct. 2, 2015.

(51) Int. Cl.
A61F 11/08 (2006.01)

(52) U.S. Cl.
CPC ......... A61F 11/08 (2013.01); A61F 2011/085 (2013.01); A61F 2250/0015 (2013.01); A61F 2250/0019 (2013.01); A61F 2250/0039 (2013.01)

(58) Field of Classification Search
CPC .... A61F 11/08; A61F 2011/085; A61F 11/10; A61F 11/12; A61F 11/14; H04R 25/02
USPC ......................................... 128/864, 866–868
See application file for complete search history.

(56) References Cited

U.S. PATENT DOCUMENTS

| 2,327,620 | A | | 8/1943 | Cole | |
|---|---|---|---|---|---|
| 2,446,707 | A | | 8/1948 | Leight | |
| 3,068,954 | A | * | 12/1962 | Strzalkowski | ....... H04R 25/556 181/135 |
| 3,080,011 | A | * | 3/1963 | Henderson | ........... H04R 25/656 181/135 |
| D207,206 | S | | 3/1967 | Geib et al. | |
| 3,415,246 | A | | 12/1968 | Hill | |
| D298,356 | S | | 11/1988 | Falco | |
| 4,807,612 | A | | 2/1989 | Carlson | |
| 5,113,967 | A | | 5/1992 | Killion et al. | |
| D330,761 | S | | 11/1992 | Falco | |
| 5,753,870 | A | * | 5/1998 | Schlaegel | ............. H04R 25/48 181/129 |
| D479,834 | S | | 9/2003 | Salazar et al. | |
| D480,386 | S | | 10/2003 | Browne et al. | |

(Continued)

FOREIGN PATENT DOCUMENTS

WO  WO 01/76520 A1  10/2001

OTHER PUBLICATIONS

International Search Report & Written Opinion dated Dec. 13, 2016 for PCT/US2016/054974.

(Continued)

Primary Examiner — Camtu T Nguyen
(74) Attorney, Agent, or Firm — Cooley LLP

(57) ABSTRACT

The present disclosure describes a cost-effective earplug device that delivers minimally distorted sound, offers sound protection, can fit most users, and can protect human hearing from dangerously-high acoustic levels without the cost or inconvenience of a custom earplug.

4 Claims, 10 Drawing Sheets

(56) References Cited

U.S. PATENT DOCUMENTS

| | | |
|---|---|---|
| D496,653 S | 9/2004 | Townsend et al. |
| D512,990 S | 12/2005 | Yang |
| D536,692 S | 2/2007 | Alwicker |
| D549,222 S | 8/2007 | Huang |
| D550,657 S | 9/2007 | Gan et al. |
| D555,150 S | 11/2007 | Christopher et al. |
| D559,836 S | 1/2008 | Lee |
| D595,272 S | 6/2009 | Kim et al. |
| D597,084 S | 7/2009 | Gondo |
| D597,534 S | 8/2009 | Christopher |
| D604,722 S | 11/2009 | Mistry |
| D622,855 S | 8/2010 | Cano, Jr. |
| D631,470 S | 1/2011 | Yoneyama et al. |
| 8,054,985 B2 | 11/2011 | Doty |
| D652,822 S | 1/2012 | Lee |
| 8,091,680 B2 | 1/2012 | Killion et al. |
| D658,157 S | 4/2012 | McManigal |
| D666,580 S | 9/2012 | Lee et al. |
| D676,026 S | 2/2013 | Lee et al. |
| D684,699 S | 6/2013 | Heaysman et al. |
| D684,700 S | 6/2013 | Heaysman et al. |
| D685,481 S | 7/2013 | Heaysman et al. |
| D705,197 S | 5/2014 | Drambarean |
| D711,356 S | 8/2014 | Yang |
| 8,848,939 B2 | 9/2014 | Keady et al. |
| D725,082 S | 3/2015 | Palmborg et al. |
| D728,107 S | 4/2015 | Torres Martin |
| D742,861 S | 11/2015 | Miyake et al. |
| 9,198,800 B2 | 12/2015 | Killion et al. |
| D764,445 S | 8/2016 | Czaniecki |
| D767,532 S | 9/2016 | Jen |
| D786,216 S | 5/2017 | Silva et al. |
| D788,079 S | 5/2017 | Son et al. |
| D799,452 S | 10/2017 | Lee |
| D801,950 S | 11/2017 | Otani et al. |
| D806,879 S | 1/2018 | Horbinski et al. |
| D808,360 S | 1/2018 | Arimoto |
| D812,042 S | 3/2018 | Xiao |
| D813,205 S | 3/2018 | Palmborg et al. |
| D817,309 S | 5/2018 | Czarniecki et al. |
| D822,646 S | 7/2018 | Dang et al. |
| D824,359 S | 7/2018 | Czarniecki |
| D827,616 S | 9/2018 | Lian |
| D841,626 S | 2/2019 | Tang |
| D842,844 S | 3/2019 | Li |
| D843,354 S | 3/2019 | Kumano |
| D845,932 S | 4/2019 | Lu |
| D846,532 S | 4/2019 | Xiao |
| D847,126 S | 4/2019 | Loermann |
| 2006/0177080 A1 | 8/2006 | Smith |
| 2009/0304220 A1 | 12/2009 | Fujikura et al. |
| 2010/0329475 A1 | 12/2010 | Killion et al. |
| 2011/0271965 A1 | 11/2011 | Parkins et al. |
| 2012/0305329 A1 | 12/2012 | Keady et al. |
| 2013/0056295 A1* | 3/2013 | Campbell ............ H04R 25/652 181/135 |
| 2013/0259286 A1 | 10/2013 | Chung et al. |
| 2014/0146989 A1 | 5/2014 | Goldstein |
| 2014/0190494 A1* | 7/2014 | Ely ........................ A61F 11/08 128/868 |
| 2014/0198926 A1 | 7/2014 | Killion et al. |
| 2015/0047651 A1 | 2/2015 | Haapapuro et al. |
| 2017/0002673 A1 | 1/2017 | Tang |

OTHER PUBLICATIONS

Supplementary European Search Report issued for Application No. EP 16 85 2773, dated Apr. 25, 2019.

* cited by examiner

DEVICE FOR PROTECTING THE HUMAN SENSORY HEARING SYSTEM WHILE RETAINING QUALITY SOUND

CROSS REFERENCE

This application claims the benefit of U.S. Provisional Application No. 62/284,496, filed Oct. 2, 2015, which is incorporated herein by reference in its entirety.

BACKGROUND

Hearing protection devices can provide hearing protection and deliver minimally distorted sounds of music and speech to a user. However, custom devices are cost prohibitive, and one-size-fits-most devices that attempt to deliver minimally distorted sound at an affordable price are often improperly used and thus do not achieve suitable levels of protection or sound quality. A one-size-fits-most hearing-protecting device that delivers minimally distorted sound, achieves optimal sound protection, is cosmetically appealing, and ensures a proper fit could offer users with a more affordable alternative to custom made products.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, the invention provides a device for attenuating a sound entering an ear of a subject, the device comprising:
  a) a first portion, wherein the first portion comprises:
    i) a sound inlet;
    ii) a face that faces an ear canal of the subject; and
    iii) a face that faces away from the ear canal of the subject,
  wherein the first portion is configured to be situated in a concha of the ear of the subject, and the sound inlet is positioned to face away from the ear canal of the subject when the device is inserted in the concha of the ear of the subject, wherein the first portion comprises a tab that curves away from the ear canal of the subject when the device is inserted in the concha of the ear of the subject;
    b) a hollow tube, wherein the hollow tube is attached to the face of the first portion that faces the ear canal of the subject, wherein the hollow tube is positioned to protrude into the ear canal of the subject when the device is inserted in the concha of the ear of the subject;
    c) a first seal, wherein the first seal has a body that has a wide end and a narrow end, and the body of the first seal tapers in size from the wide end to the narrow end, wherein the first seal contains an aperture that is about circular through which the hollow tube protrudes, and wherein the first seal fits over the hollow tube at a point that is proximal to the face of the first portion that faces the ear canal, wherein the first seal is situated at about the opening of the ear canal of the subject when the device is inserted in the concha in the ear of the subject; and
    d) a second seal, wherein the second seal fits over the hollow tube at a point that is more distal from the first portion than the point at which the first seal fits over the hollow tube, wherein the second seal comprises an open terminus that is situated inside of the ear canal of the subject when the device is inserted in the concha of the ear of the subject,
  wherein the hollow tube is flexible and is positioned to fit inside the ear canal of the subject, and the hollow tube houses a sound bore, and
  wherein the sound bore, the sound inlet, and the open terminus together form a continuous passage that carries sound from outside the ear to inside the ear when the device is inserted in the concha of the ear of the subject.

In some embodiments, the invention provides a method of attenuating a sound entering an ear of a subject, the method comprising inserting into the ear of the subject a device, the device comprising:
  a) a first portion, wherein the first portion comprises:
    i) a sound inlet;
    ii) a face that faces an ear canal of the subject; and
    iii) a face that faces away from the ear canal of the subject,
  wherein the first portion is inserted in a concha of the ear of the subject, and the sound inlet is positioned to face away from the ear canal of the subject, wherein the first portion comprises a tab that curves away from the ear canal of the subject;
    b) a hollow tube, wherein the hollow tube is attached to the face of the first portion that faces the ear canal of the subject, wherein the hollow tube is positioned to protrude into the ear canal of the subject;
    c) a first seal, wherein the first seal has a body that has a wide end and a narrow end, and the body of the first seal tapers in size from the wide end to the narrow end, wherein the first seal contains an aperture that is about circular through which the hollow tube protrudes, and wherein the first seal fits over the hollow tube at a point that is proximal to the face of the first portion that faces the ear canal, wherein the first seal is situated at about the opening of the ear canal of the subject; and
    d) a second seal, wherein the second seal fits over the hollow tube at a point that is more distal from the first portion than the point at which the first seal fits over the hollow tube, wherein the second seal comprises an open terminus that is situated inside of the ear canal of the subject,
  wherein the hollow tube is flexible and is positioned inside the ear canal of the subject, and the hollow tube houses a sound bore, and
  wherein the sound bore, the sound inlet, and the open terminus together form a continuous passage that carries sound from outside the ear to inside the ear of the subject.

DETAILED DESCRIPTION

Figure 1:
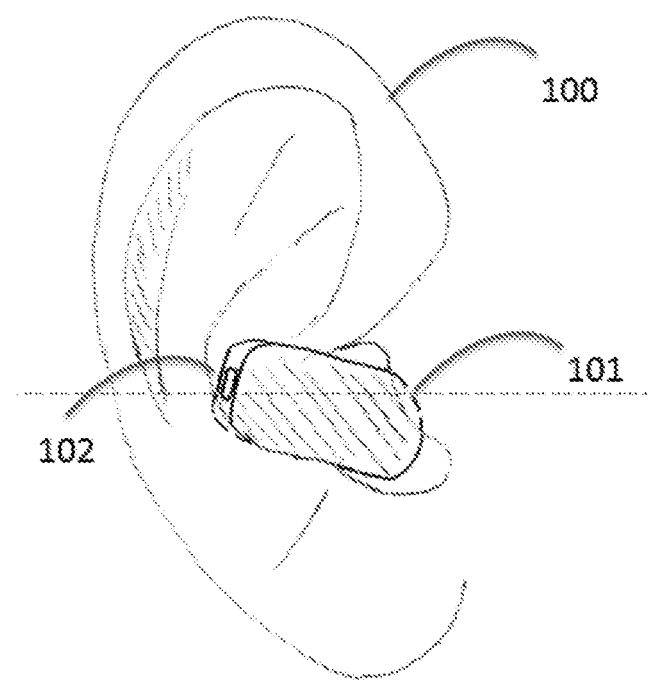
FIG. 1 is a side view of the present invention in the human ear.

Many types of foam and elastic materials are used to produce pre-molded and custom hearing protection devices. High quality earplugs are comfortable, but are expensive because custom molding is required. One-size-fits-most earplugs that are cosmetically appealing and attempt to deliver minimally-distorted sound at an affordable price are often improperly used and thus fail to achieve suitable levels of protection or deliver minimally distorted sound.

The disclosed invention describes a cost-effective earplug device that delivers minimally-distorted sound, offers sound protection, can fit most users, is cosmetically appealing, and can protect human hearing from dangerously high acoustic levels without the cost or inconvenience of a custom earplug. In some embodiments, the invention can attenuate environmental sounds to a safe level, for example, typically less than 85 dB sound pressure levels in the ear.

The invention is a device comprising an intracanal sealing system and an integral external concha tab that can achieve a desired level of attenuation at a regulated depth of insertion. The sealing system described herein provides enhanced attenuation of sound and minimizes acoustical distortion caused by the presence of the device in the ear compared to other designs. The invention further comprises an acoustic resonance channel tube, which allows sound to reach the tympanic membrane and maintain sound quality appropriate for listening to music and speech. The invention further comprises the use of elastomeric materials to achieve proper fit, retention, and comfort.

The disclosed invention comprises a main body piece that is positioned to fit in the concha of the human ear. In some embodiments, the external hardware piece is used to move the internal portion of the device into the ear canal, allowing for proper placement of the device and sound inlet. Once inserted, the internal portion of the device contacts the canal and holds the device in place. In some embodiments, the main body piece can also prevent the user from intentionally or unintentionally inserting the device too deeply. In some embodiments, the external hardware piece is used to remove the entire device from the ear. In some embodiments, the invention fits a concha that is about 15 mm, about 16 mm, about 17 mm, about 18 mm, about 19, or about 20 mm wide. In some embodiments, the invention fits a concha that is about 15 mm wide. In some embodiments, the invention fits a concha that is about 17.5 mm wide. In some embodiments, the invention fits a concha that is about 20 mm wide.

In some embodiments, the invention fits a concha that is about 10 mm, about 11 mm, about 12 mm, about 13 mm, about 14 mm, or about 15 mm deep. In some embodiments, the invention fits a concha that is about 11 mm deep. In some embodiments, the invention fits a concha that is about 13 mm deep. In some embodiments, the invention is modified to fit conchas of different sizes, for example, the device can be modified to fit the average size of a child's concha.

In some embodiments, the main body of the device is made of a hard plastic, such as acrylonitrile butadiene styrene (ABS) plastic. In some embodiments, the main body is made of a soft material, such as silicone overmolding, soft silicone, or a thermoplastic elastomer. In some embodiments, the main body is made of only hard plastic. In some embodiments, the main body is made of only soft silicone. In some embodiments, the main body is made of a combination of hard plastic and soft silicone. In some embodiments, the main body comprises a stamped metal or alloy logo, such as a stamped copper logo. In some embodiments, the main body comprises a stamped indication of fit to the right ("R") or left ("L") ear.

In some embodiments, the main body piece is about 10 mm, about 11 mm, about 12 mm, about 13 mm, about 14 mm, about 15 mm, about 16 mm, about 17 mm, about 18 mm, about 19 mm, or about 20 mm long. In some embodiments the main body piece is about 13 mm, about 14 mm, about 15 mm, or about 16 mm long. In some embodiments, the main body piece is about 15.86 mm long. In some embodiments, the main body piece is about 8 mm, about 9 mm, about 10 mm, about 11 mm, about 12 mm, about 13 mm, about 14 mm, or about 15 mm tall. In some embodiments, the main body piece is about 11 mm, about 12 mm, or about 13 mm tall. In some embodiments, the main body piece is about 11.70 mm tall. In some embodiments, the main body piece is modified to different sizes, for example, the device can be modified to fit the average size of a child's concha and ear canal.

The invention also comprises a sound inlet that receives environmental sounds. The sound inlet, which is contiguous with a sound bore, is larger in diameter than the diameter of the sound bore. The sound inlet transmits sound to the tympanic membrane. In some embodiments, the sound bore is about 2 mm, about 3 mm, about 4 mm, or about 5 mm wide. In some embodiments, the sound inlet is about 3 mm or about 4 mm wide. In some embodiments, the sound bore is about 3.04 mm wide.

The sound bore is an acoustic resonantor for resonant sounds of about 2 kHz, about 3 kHz, about 4 kHz, about 5 kHz, about 6 kHz, about 7 kHz, or about 8 kHz. In some embodiments, the sound bore is designed to be an acoustic resonator for resonant sounds that are about 2 kHz. In some embodiments, the sound bore is designed to be an acoustic resonator for resonant sounds that are about 3 kHz. In some embodiments, the sound bore is designed to be an acoustic resonator for resonant sounds that are about 4 kHz. In some embodiments, the sound bore is designed to achieve acoustic resonance from about 2.5 kHz to about 2.8 kHz. In some embodiments, the sound bore is designed to achieve acoustic resonance from about 2.6 kHz to about 2.7 kHz. In some embodiments, the sound bore is designed to achieve acoustic resonance at about 2.7 kHz.

In some embodiments, the sound bore is about 25 mm, about 26 mm, about 27 mm, about 28 mm, about 29 mm, about 30 mm, about 31 mm, about 32 mm, about 33 mm, about 34 mm, or about 35 mm long. In some embodiments, the sound bore is about 25 mm long. In some embodiments, the sound bore is about 30 mm long. In some embodiments, the sound bore is about 33 mm long. In some embodiments, the sound bore is about 35 mm long. In some embodiments, the sound bore is made of a polyvinyl chloride-type plastic. In some embodiments, the sound bore is molded into the main body piece.

The sound bore of the device can be bent or kinked such that the device does not protrude from the ear. In some embodiments, the sound bore has a kink that is about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm from the sound inlet. In some embodiments, the sound bore has a kink that is about 16 mm or about 17 mm from the sound inlet. In some embodiments, the sound bore has a kink that is about 16.5 mm from the sound inlet.

In some embodiments, the sound bore is cased in a flexible hollow tube. In some embodiments, the flexible hollow tube is straight. In some embodiments, the flexible hollow tube is curved. In some embodiments, the flexible hollow tube is curved and assures proper depth placement of the device. In some embodiments, the flexible hollow tube is held by the main body piece and is tucked under the antitragus, which assures a cosmetic appeal, proper depth placement, and secure placement of the earpiece. In some embodiments, the flexible hollow tube is positioned by the external hardware to orient toward the direction of incoming sound. In some embodiments, the flexible hollow tube is about 10 mm, about 11 mm, about 12 mm, about 13 mm, about 14 mm, or about 15 mm long. In some embodiments, the flexible hollow tube is about 10 mm, about 11 mm, or about 12 mm long. In some embodiments, the flexible hollow tube is about 11.42 mm long.

The hollow tube can connect to a face of the external portion of the device that is directed toward the ear canal when in use. The hollow tube can be disposed to the face at an angle that is, for example, at least 45 degrees, at least 50 degrees, at least 55 degrees, at least 60 degrees, at least 65 degrees, at least 70 degrees, at least 75 degrees, at least 80 degrees, at least 85 degrees, about 45 degrees, about 50 degrees, about 55 degrees, about 60 degrees, about 65 degrees, about 70 degrees, about 75 degrees, about 80 degrees, about 85 degrees, or about 90 degrees. For example, the hollow tube can be about perpendicular to the face, or within about 5 degrees, about 10 degrees, about 15 degrees, about 20 degrees, or about 25 degrees of perpendicularity.

The disclosed invention further comprises an outer seal that is sized and shaped to fit the entry portion of most human ear canals. The outer seal is sized to fit an average-sized ear canal that is about 20 mm, about 21 mm, about 22 mm, about 23 mm, about 24 mm, about 25 mm, about 26 mm, about 27 mm, about 28 mm, about 29 mm, or about 30 mm in length. In some embodiments, the outer seal is sized to fit an ear canal that is about 20 mm in length. In some embodiments, the outer seal is sized to fit an ear canal that is about 25 mm in length. In some embodiments, the outer seal is sized to fit an ear canal that is about 30 mm in length.

In some embodiments, the outer seal is sized and shaped to fit the oval opening of an ear canal that is about 12 mm×about 10 mm. In some embodiments, the outer seal is sized and shaped to fit the oval opening of an ear canal that is about 9 mm×about 6.5 mm. In some embodiments, the outer seal is about 15 mm×about 15 mm in size and is compressible such that the concha can prevent over-insertion of the device into the ear canal. In some embodiments, the outer seal is about 13 mm×about 10 mm in size and is compressible to prevent over insertion into the ear canal. In some embodiments, the outer seal is about 12.4 mm×about 9.2 mm in size and is compressible to prevent over insertion into the ear canal.

The disclosed invention further comprises an inner seal that is connected to the outer seal by the flexible tube, which also encloses the sound bore. The inner seal provides additional sound attenuation and seals the deeper portion of the ear canal to minimize the occlusion effect. The occlusion effect occurs when an object fills the outer portion of a person's ear canal, and that person perceives booming echo-sounds of their own voice.

The inner seal can be positioned at the end of the sound bore and allows sound to enter the volume between the inner seal and the tympanic membrane. In some embodiments, the seal is made from very pliable and soft elastomeric material. In some embodiments, the seal is made from soft silicone. In some embodiments, the seal is made from a thermoplastic polymer. In some embodiments, the seal of made from a thermoplastic polymer such as solid or open foam (i.e., open cell or closed cell polymers).

The disclosed invention can utilize a dual-sealing mechanism. The outer seal of the device described herein can be denser and harder than the inner seal of the device. The denser more rigid outer seal of the device can provide superior sound attenuation of foam or pre-molded elastomer semicircular features. The inner seal can be made of a softer material that can sit comfortably in the ear canal. In some embodiments, the ratio of the hardness or density of the outer seal to the density of the inner seal is about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, or about 20:1. In some embodiments, the ratio of the density of the outer seal to the density of the inner seal is about 4:1.

In some embodiments, the described invention can comprise friction fit silicone tips that act as additional seals. In some embodiments, the invention comprises friction fit silicone tips with 1, 2, or 3 seals. In some embodiments, the invention comprises a friction fit silicone tip with one seal. In some embodiments, the invention comprises a friction fit silicone tip with two seals. In some embodiments, the invention comprises a friction fit silicone tip with three seals.

In some embodiments, the friction fit silicone tip is about 10 mm, about 11 mm, about 12 mm, about 13 mm, about 14 mm, about 15 mm, about 16 mm, about 17 mm, about 18 mm, about 19 mm, or about 20 mm long. In some embodiments, the friction fit silicone tip is about 15 mm, about 16 mm, about 17 mm, or about 18 mm long. In some embodiments, the friction fit silicone tip is about 17.39 mm long. In some embodiments, the friction fit silicone tip that acts as the inner seal is about 5 mm, about 6 mm, about 7 mm, about 8 mm, about 9 mm, or about 10 mm deep. In some embodiments, the friction fit silicone tip that acts as the inner seal is about 5 mm, about 6 mm, or about 7 mm deep. In some embodiments, the friction fit silicone tip is about 6.21 mm deep.

The invention also comprises an attenuating filter that is located near the inner seal of the device. The attenuating filter is made of a semi-permeable material that can reflect some portion of the sound, and allows some sound to pass through the filter. The reflected sound provides via the sound bore a quarter wave resonant cavity. The attenuating filter further tunes the acoustic frequencies and achieves a more realistic sound quality. The attenuating filter also provides acoustic resistance and thus provides a secondary feature to the sound bore. The distance from the sound inlet to the tympanic membrane provides one resonant peak, and the distance from the sound inlet to the attenuating filter provides a second resonant peak. In some embodiments, the second resonant peak is the dominant peak.

An attenuating filter made of acoustically-resistant material can allow the user to fine tune the overall sound quality of the device. In some embodiments, the attenuating filter is made of fine wool, fine beads of metal or polymer material fused to form a plug, or a polymer strand weaved material.

In some embodiments, the attenuating filter is made from another material that is intended to filter the acoustic sound.

The attenuating filter of the disclosed invention can be large enough to cover the entire opening of the sound bore. In some embodiments, the attenuating filter is about 1 mm, about 2 mm, or about 3 mm in diameter and about 1 mm, about 2 mm, or about 3 mm tall. In some embodiments, the attenuating filter is about 1 or about 2 mm in diameter and about 1 mm or about 2 mm tall. In some embodiments, the attenuating filter is about 1.53 mm in diameter and about 1.88 mm tall.

In some embodiments, the described device can be about 20 mm, about 21 mm, about 22 mm, about 23 mm, about 24 mm, about 25 mm, about 26 mm, about 27 mm, about 28 mm, about 29 mm, or about 30 mm long. In some embodiments, the described device can be about 24 mm, about 25 mm, about 26 mm, about 27 mm, or about 28 mm long. In some embodiments, the described device can be about 26.55 mm long. In some embodiments, the described device can be about 20 mm, about 21 mm, about 22 mm, about 23 mm, about 24 mm, or about 25 mm wide. In some embodiments, the described device can be about 22 mm, about 23 mm, or about 24 mm wide. In some embodiments, the described device can be about 23.79 mm wide. In some embodiments, the described device can be about 15 mm, about 16 mm, about 17 mm, about 18 mm, about 19 mm, or about 20 mm deep. In some embodiments, the described device can be about 15 mm, about 16 mm, or about 17 mm deep. In some embodiments, the described device can be about 16.24 mm deep.

The disclosed invention can attenuate environmental sound levels to safe levels. In some embodiments, the device can be used to attenuate environmental sounds that are up to about 200 dB, up to about 190 dB, up to about 180 dB, up to about 170 dB, up to about 160 dB, up to about 150 dB, up to about 140 dB, up to about 130 dB, up to about 125 dB, up to about 120 dB, up to about 115 dB, up to about 110 dB, up to about 105 dB, up to about 100 dB, up to about 95 dB, up to about 90 dB, up to about 85 dB, up to about 80 dB, up to about 75 dB, up to about 70 dB, up to about 65 dB, up to about 60 dB, up to about 55 dB, or up to about 50 dB. In some embodiments, the device can attenuate the environmental sound by about 50%, about 45%, about 40%, about 35%, about 30%, about 25%, about 20%, about 15%, about 10%, or about 5%. In some embodiments, the device can attenuate the environmental sound by about 1 dB, about 2 dB, about 3 dB, about 4 dB, about 5 dB, about 10 dB, about 15 dB, about 20 dB, about 25 dB, about 26 dB, about 27 dB, about 28 dB, about 29 dB, about 30 dB, about 35 dB, about 40 dB, about 45 dB, or about 50 dB. In some embodiments, the frequency of the sound being attenuated is about 100 Hz, about 125 Hz, about 150 Hz, about 175 Hz, about 200 Hz, about 300 Hz, about 400 Hz, about 500 Hz, about 600 Hz, about 700 Hz, about 800 Hz, about 900 Hz, about 1000 Hz, about 1250 Hz, about 1500 Hz, about 1750 Hz, about 2000 Hz, about 2250 Hz, about 2500 Hz, about 2750 Hz, about 3000 Hz, about 3250 Hz, about 3500 Hz, about 3750 Hz, about 4000 Hz, about 4250 Hz, about 4500 Hz, about 4750 Hz, about 5000 Hz, about 5250 Hz, about 5500 Hz, about 5750 Hz, about 6000 Hz, about 6250 Hz, about 6500 Hz, about 6750 Hz, about 7000 Hz, about 7250 Hz, about 7500 Hz, about 7750 Hz, or about 8000 Hz.

In some embodiments, the disclosed invention can attenuate the environmental sound by about 25 dB across frequencies from about 125 to 8000 Hz. In some embodiments, the disclosed invention can attenuate the environmental sound by about 15 dB across frequencies from about 125 to 8000 Hz. In some embodiments, the disclosed invention can attenuate the environmental sound by about 25 dB across frequencies from about 500 to 3000 Hz. In some embodiments, the disclosed invention can attenuate the environmental sound by about 15 dB across frequencies from about 500 to 3000 Hz. In some embodiments, the disclosed invention can attenuate the environmental sound by about 25 dB across frequencies from about 1000 to 3000 Hz. In some embodiments, the disclosed invention can attenuate the environmental sound by about 15 dB across frequencies from about 1000 to 3000 Hz.

EXAMPLES

Features of the Invention

FIG. 1 depicts a side view of the present invention in the human ear. The tragus and antitragus of the pinna 100 of the human ear partially occlude the invention. The tragus is a small cartilaginous flap that covers the ear canal. The device is positioned in the concha of the human ear by feature 101. The concha is a bowl-shaped feature within the pinna 100 and adjacent to the ear canal. The dimensions of the concha can vary from user to user, but the average diameter of the concha is about 15 mm to about 20 mm (0.6 in to 0.8 in) and the average depth is approximately 13 mm (0.5 in). The user can press the device into the ear without regard for over insertion by feature 101. The sound inlet 102 receives environmental sounds and is contiguous with the path of the acoustical sound bore 107, depicted in FIGS. 3 and 4, which transmits sound to the tympanic membrane.

Figure 2:
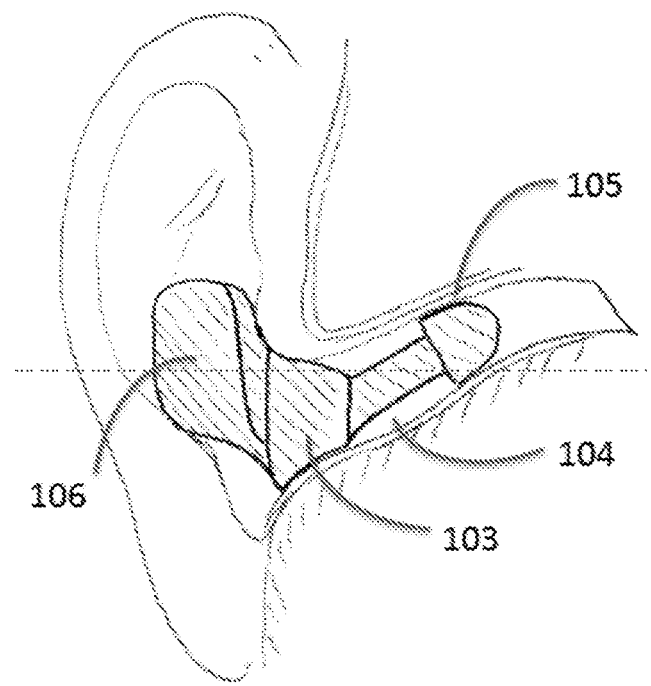
FIG. 2 is a cross sectional view of the present invention inserted into the human ear canal.
Figure 3:
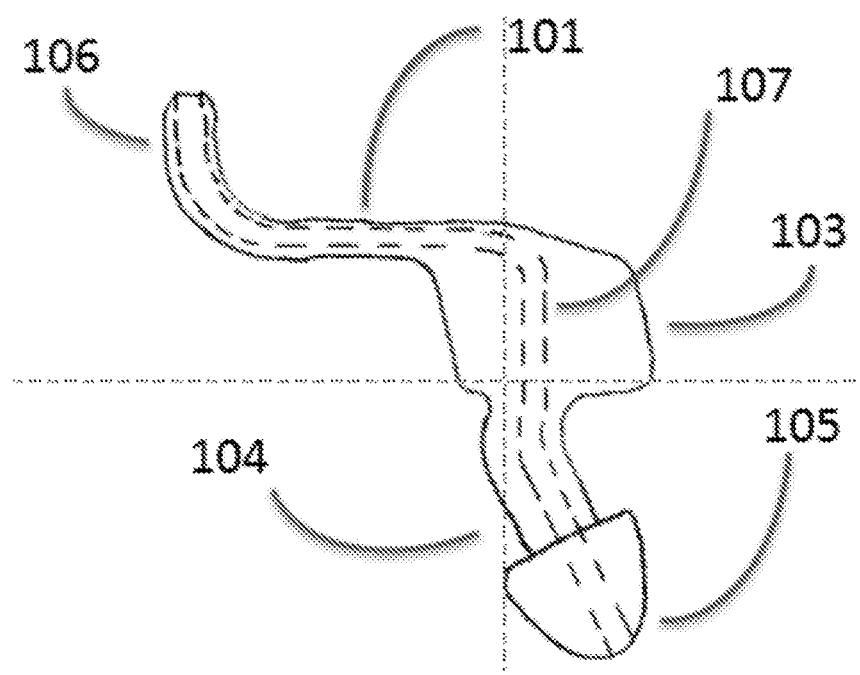
FIG. 3 is a top-down view of the present invention with integrated sound bore.
Figure 4:
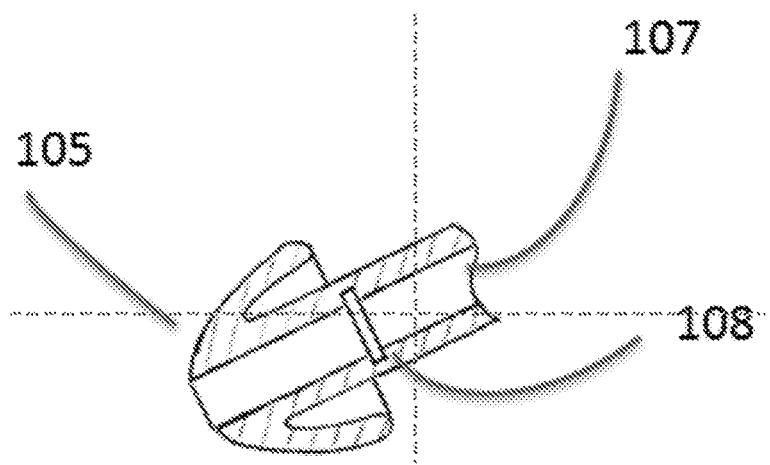
FIG. 4 is a cross sectional view of the inner seal portion and attenuation filter of the present invention.

FIG. 2 illustrates a cross sectional view of the outer ear canal and pinna of the human ear and the present invention. The ear canal (auditory canal; external auditory meatus) is an "S" shaped duct, which provides an access route for acoustic waves to travel to the tympanic membrane. The average length of an adult ear canal is approximately 25 mm (1.0 in) with a standard deviation of approximately 2 mm (0.2 in), and is approximately 5% longer in males than in females. The shape and cross sectional dimensions of the ear canal change along the length. The oval opening of the canal has average dimensions of about 9 mm (0.4 in) by about 6.5 mm (0.3 in), and the canal becomes narrower along the length. The outer seal 103 is sized and shaped to fit in most human canals. The outer seal 103 is limited in length and is conical to generally match the contour of the ear canal prior to the second bend. The shape (ovoid), size (major axis 12.4 mm by minor axis 9.2 mm), and compressibility of 103 prevents over-insertion in most human ear canals. Additional sizes, shapes, and compressibility can be used to fit various users depending on size and preferences. A flexible tube 104 joins the inner seal 105 to the outer seal 103. 104 is a hollow member that is a part of the sound bore 107 (FIGS. 3 and 4). The inner seal 105 provides additional sound attenuation and seals the deeper portion, also referred to as the bony section of the ear canal, to minimize the occlusion effect. Because 105 is positioned deep in the ear, 105 is made from a very pliable and soft elastomeric material. 105 also is the termination for acoustical sound bore 107 (FIGS. 3 and 4), allowing sound to enter the volume between 105 and the tympanic membrane. 106 is a portion of 101 that is designed to incorporate the sound inlet port 102, and to orient the port forward in the direction of incoming sound. 102 can be located and oriented in other aspects of 101 or 106 to desired shape or to tune incoming sound.

FIG. 3 illustrates the path of the sound bore 107 (dotted line) through the present invention. 107 is designed to be an acoustical resonator, and more specifically, of resonant sound in the 2-4 kHz range. For example, a channel length of 33 mm can achieve acoustical resonance at 2700 Hz. If 107 were instead a straight tube, the tube could protrude from the ear canal in an awkward manner, but more importantly, a straight tube can be dangerous in that any blow to the head could drive the earpiece too deep into the ear canal. By incorporating sound bore 107 into 101, the present invention achieves both the appropriate length in an aesthetically-appealing manner with the additional benefit of providing features that assure proper depth placement of the inventive device. Features 106 and 101 have the additional benefit that for most user's ears, 106 is tucked under the antitragus and 101 is tucked under the tragus. This configuration provides additional assurance that the earpiece will not dislodge and fall out of the user's ear.

In more detail, 106 is a portion of the 101 tab. Portion 106 is designed to curve along the inferior portion of the concha such that it presents the sound inlet 102 in the direction of incoming sound. Preferably, sound directly in front of the person is usually of greatest interest. 106 is also mechanically-integrated with 101, 103, 104, and 105 such that 106 can be used by the user to remove the entire device from the ear. A user can easily grip and withdraw the entire ear plug by displacing the antitragus slightly to gain access to 106 and then grasping 106 between thumb and index finger.

The sound bore 107 prevents acoustical normal resonance. This feature can be beneficial for any ear plug that resides in the ear canal. 107 provides a key feature in achieving attenuated but unadulterated sound perception. 107 can be molded into the earpiece or can be formed by molding an extruded or injection molded tube into the housing that incorporates 101, 103, 104, and 105. 107 can be a singular channel as shown, or as multiple channels. For example, the channel bore, or multiple channels, can have an effective cross sectional area of 2.5 mm$^2$. The cross sectional area can be increased to allow greater mid-frequencies, or can be decreased to allow fewer mid-frequencies, through to the ear.

FIG. 4 shows the incorporation of an attenuating filter 108 located near or in the inner seal 105. The attenuating filter 108 further tunes the acoustical frequencies to achieve a flatter, more realistic quality of sound. 108 also provides acoustical resistance and thus, provides a secondary feature to the sound bore 107 so that the distance from the sound inlet 102 to the tympanic membrane provides one resonant peak, and the distance from the sound inlet 102 to the attenuating filter 108 provides a second resonant peak. Judicious use of an acoustically resistant material in 108 allows tuning of the overall sound quality of the device. 108 can be made from fine wool, fine beads of metal or polymer material fused to form a plug, or a polymer strand weaved material, or other materials intended to filter the acoustic signal.

Figure 5:
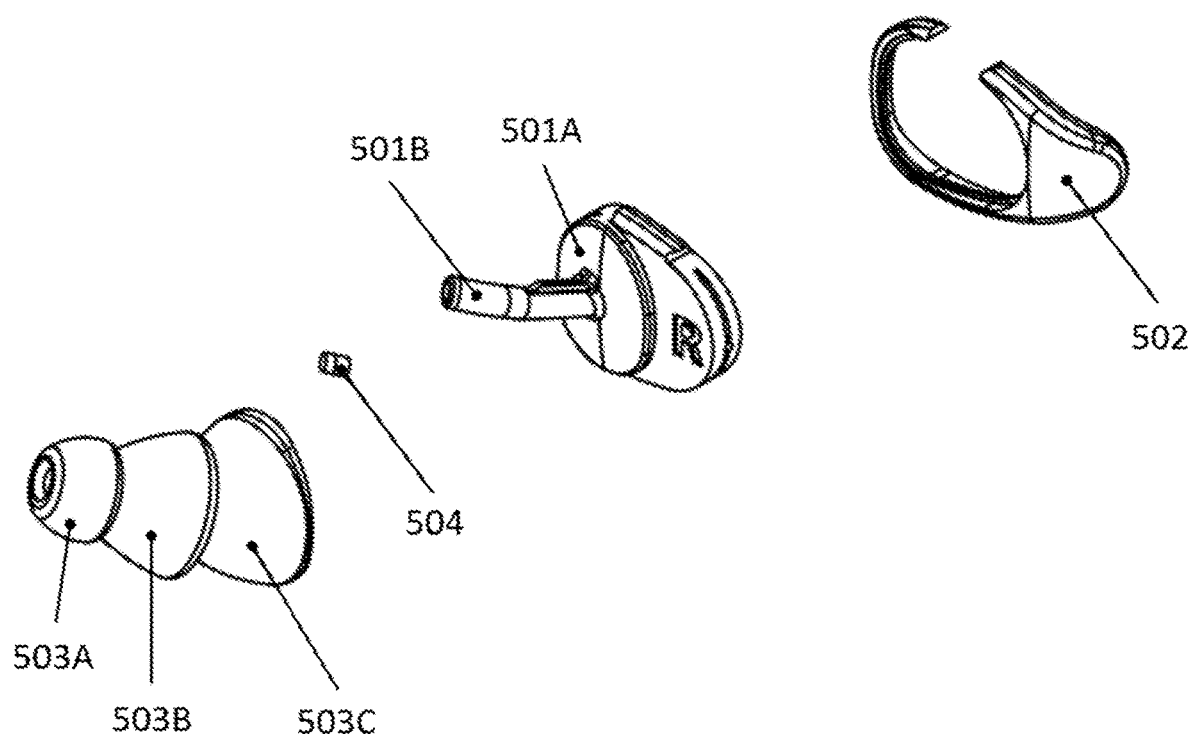
FIG. 5 depicts an embodiment of the present invention.

FIG. 5 depicts an exploded view of an embodiment of the present invention, which includes a main unit 501A, a sound bore 501B, a sound inlet 502, an inner seal 503A, a middle seal 503B, an outer seal 503C, and an attenuating filter 504. The sound inlet 502 attaches to the outer frame of the main unit 501A, which then allows environmental sounds to travel to the device via main unit 501A and sound bore 501B. The attenuating filter 504 is located within the sound bore 501B and is configured to filter the incoming sound. The inner seal 503A, the middle seal 503B, and the outer seal 503C attach to the main unit by encapsulating the sound bore 501B. The seal can be made of flexible plastic material to fit the contour of the ear canal and to minimize or prevent environmental sounds from directly entering the ear canal.

Figure 6:
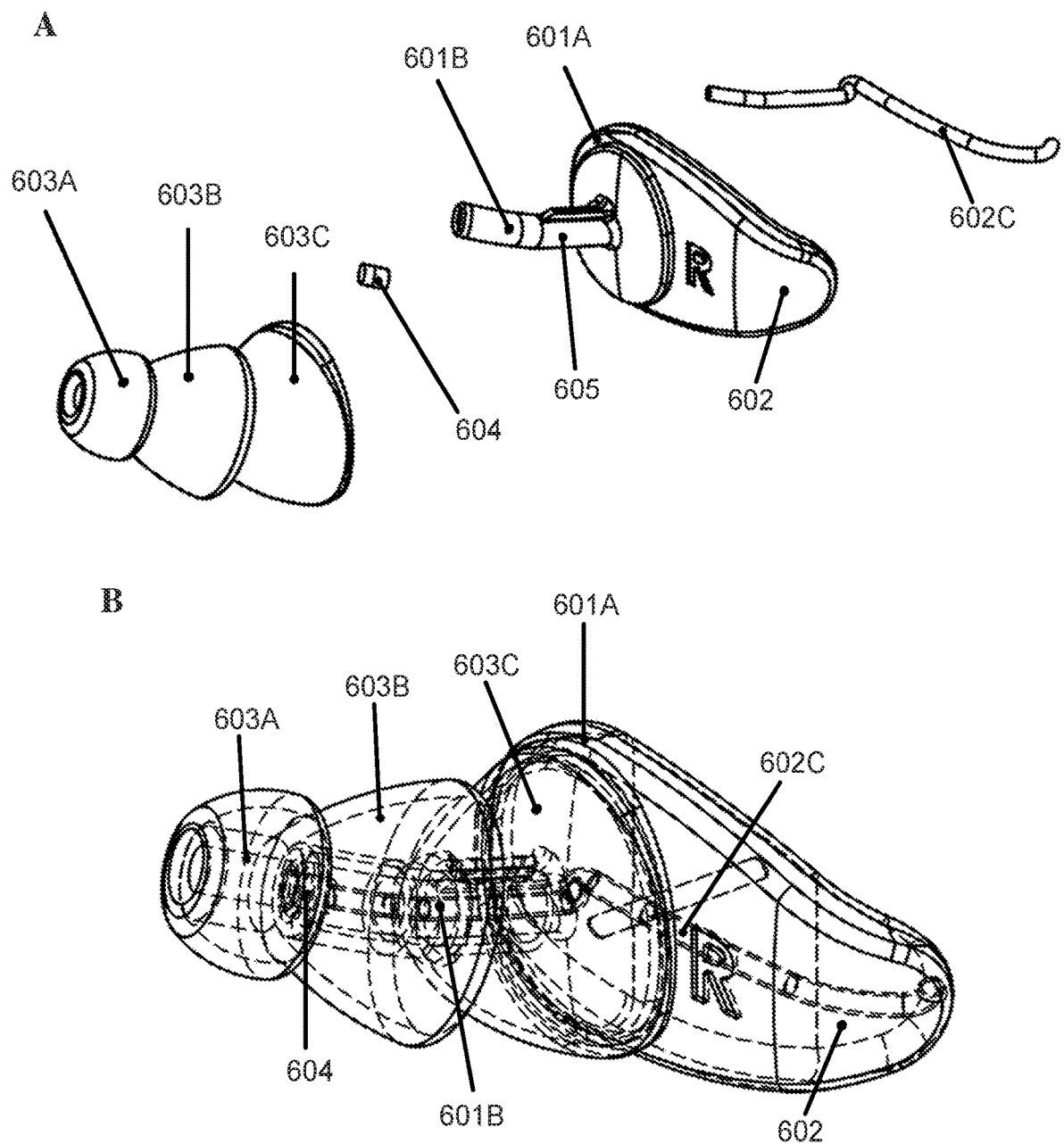
FIG. 6 depicts an embodiment of the present invention at panels A and B.

FIG. 6 at panel A depicts an exploded view of an embodiment of the present invention, which includes a main unit 601A comprising a sound inlet 602 and a first sound bore 601B, and a second sound bore 602C, an inner seal 603A, a middle seal 603B, an outer seal 603C, a hollow tube 605, and an attenuating filter 604. The second sound bore 602C is internally attached to the main unit 601A and controls the frequency of the environmental sounds that enter the device via main unit 601A and first sound bore 601B. The cross sectional area of 602C can be increased to allow greater mid-frequencies, or can be decreased to allow fewer mid-frequencies, through to the ear. The attenuating filter 604 is located within the first sound bore 601B and is configured to filter the incoming sound. The inner seal 603A, the middle seal 603B, and the outer seal 603C attach to the main unit by encapsulating the first sound bore 601B. FIG. 6 at panel B depicts an overlay of an embodiment of the present invention.

Figure 7:
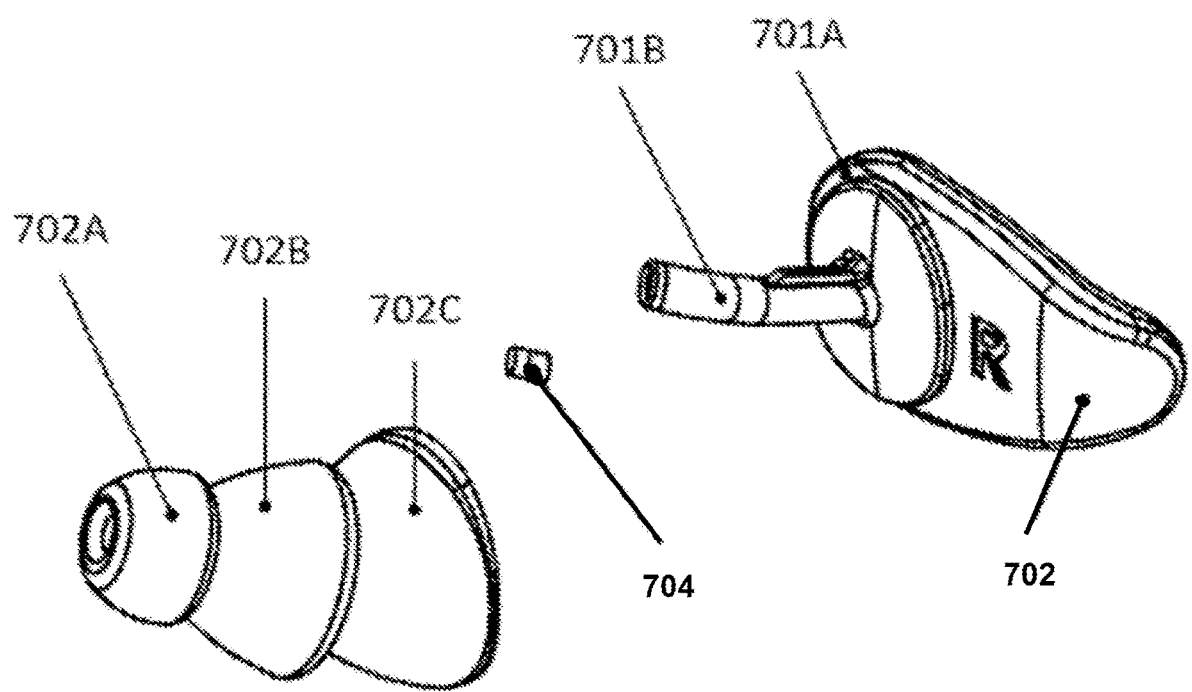
FIG. 7 depicts an embodiment of the present invention.

FIG. 7 depicts an exploded view of an embodiment of the present invention, which includes a main unit 701 comprising a sound inlet 702 and a sound bore 701B, an inner seal 702A, a middle seal 702B, an outer seal 702C, and an attenuating filter 704. The attenuating filter 704 is located within the sound bore 701B and is configured to filter the incoming sound. The inner seal 703A, the middle seal 703B, and the outer seal 703C attach to the main unit by encapsulating the sound bore 701B.

Figure 8:
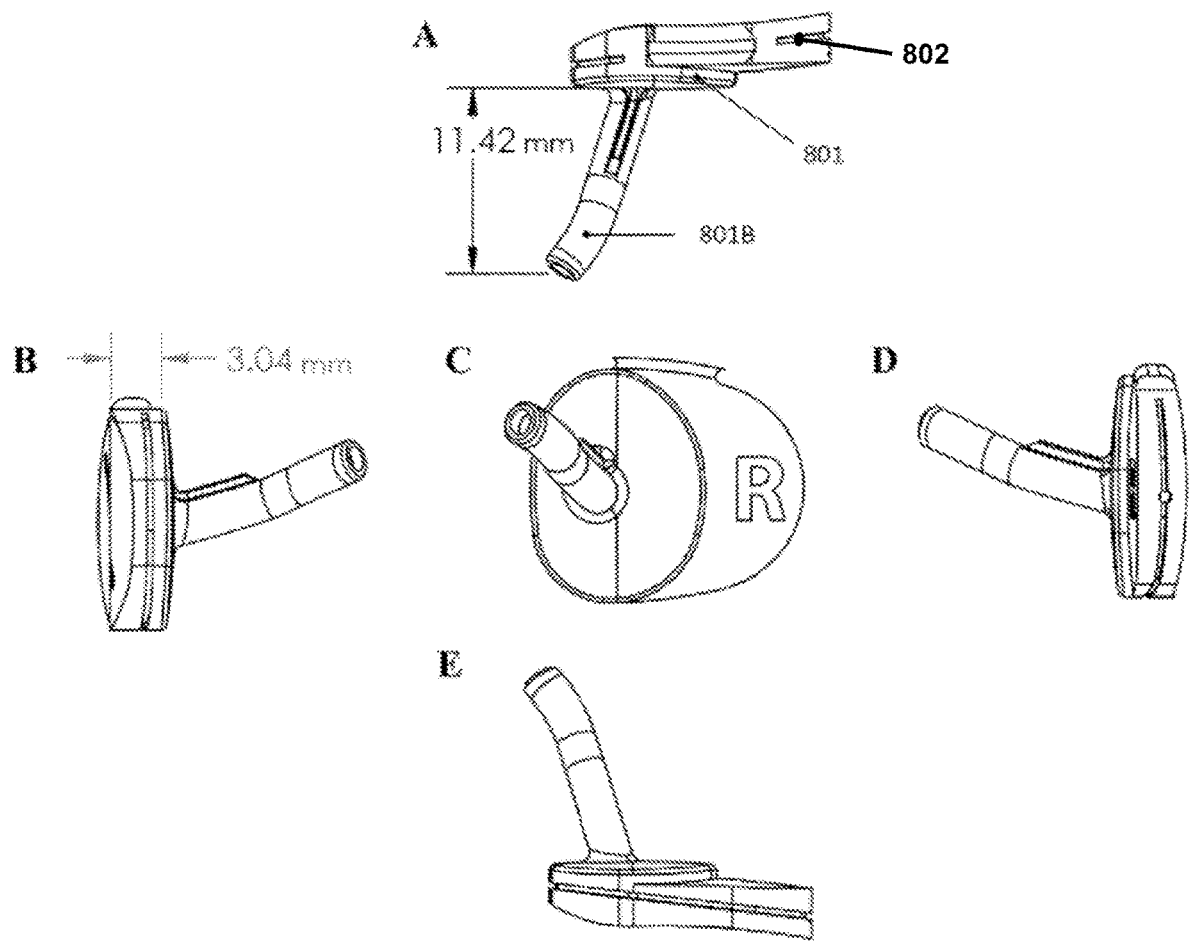
FIG. 8 illustrates cross sectional views of the main unit of an embodiment of the present invention at panels A-E.

FIG. 8 at panels A-E illustrates cross sectional views of the main unit 801 of an embodiment of the present invention, which comprises a sound inlet 802 and a sound bore 801B. The length of the sound bore 801B is 11.42 mm and the width of the sound inlet 801A is 3.04 mm.

Figure 9:
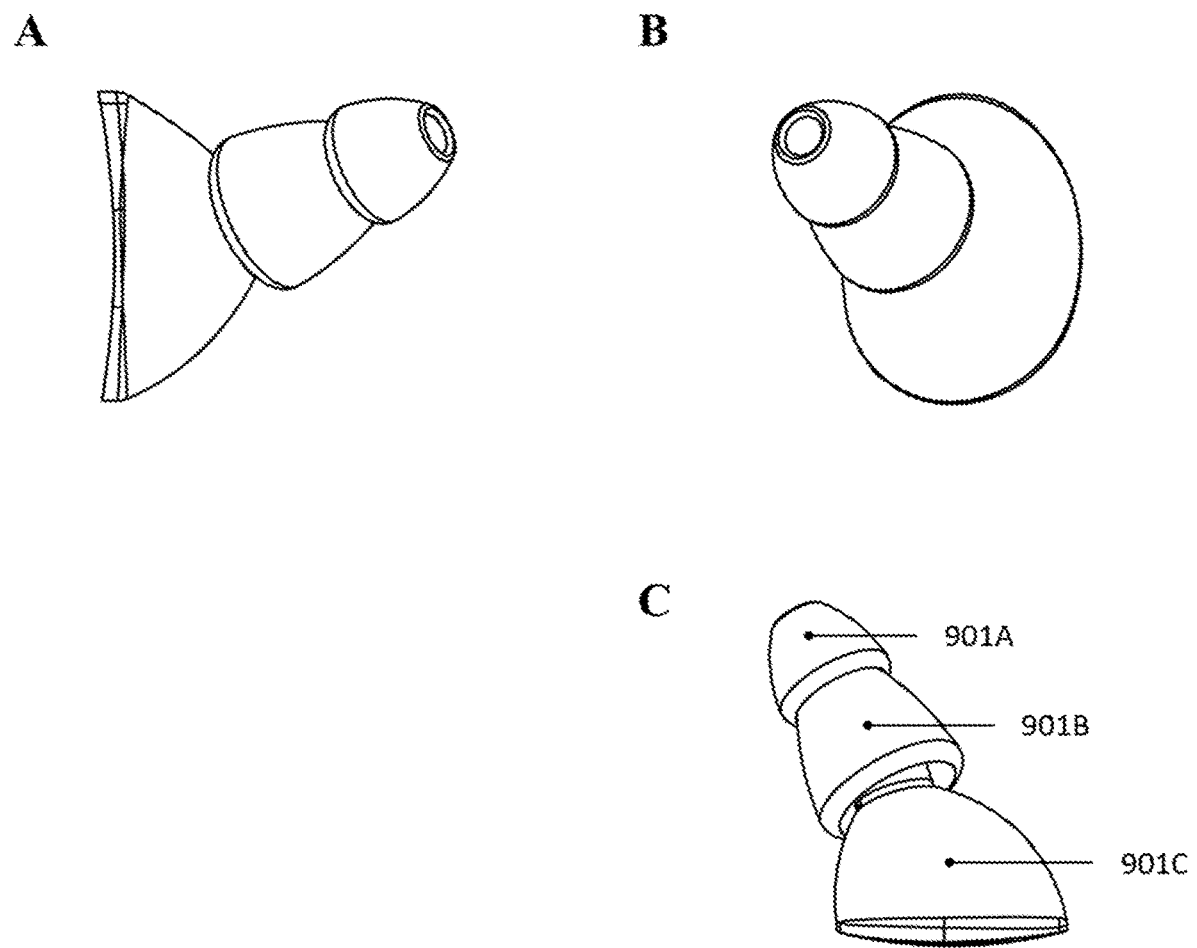
FIG. 9 illustrates cross sectional views of a small version of the inner, middle, and outer seal of an embodiment of the present invention at panels A-C.

FIG. 9 at panels A-C illustrates cross sectional views of the small version of the inner seal 901A, middle seal 901B, and outer seal 901C, which position the present invention onto the ear canal of the user.

Figure 10:
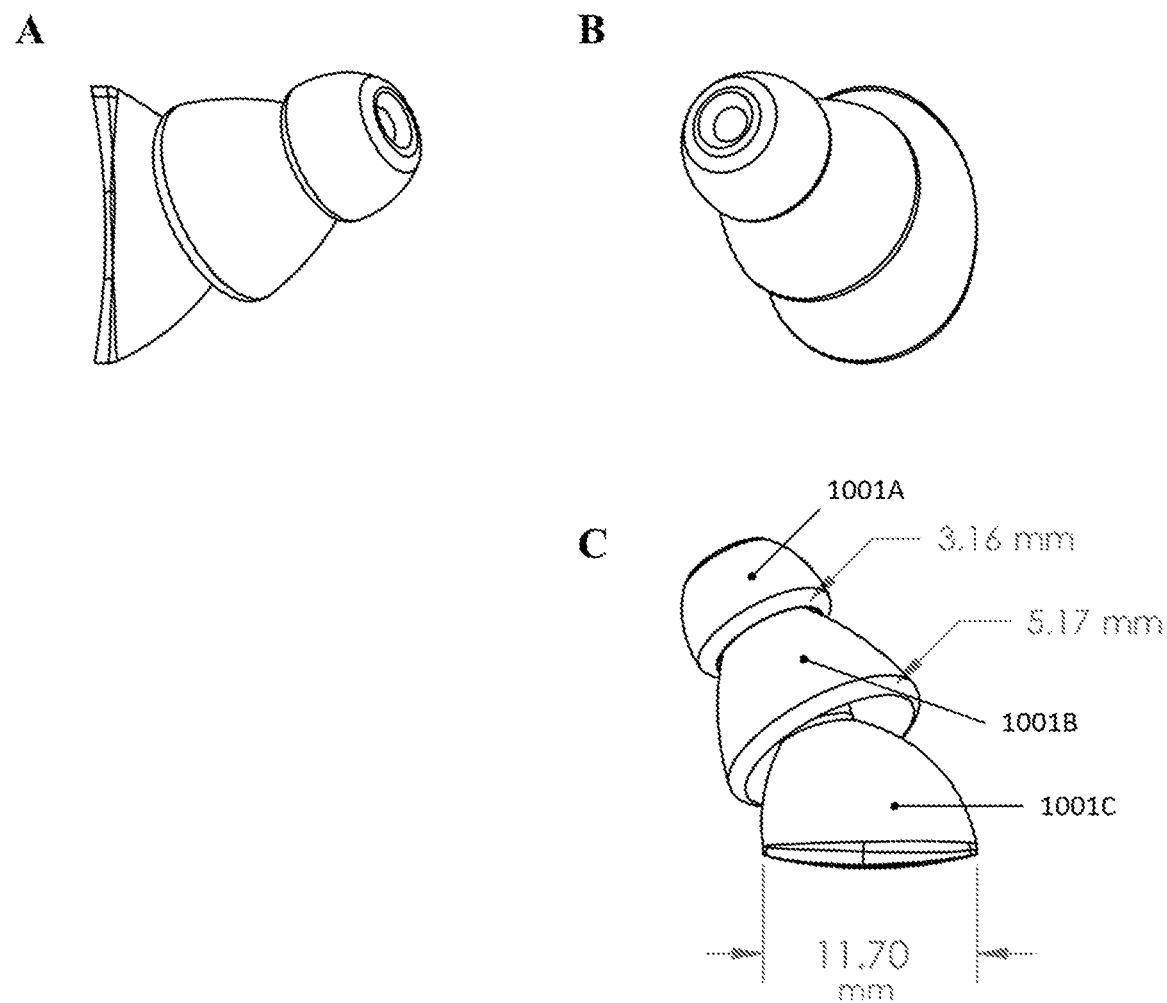
FIG. 10 illustrates cross sectional views of a large version of the inner, middle, and outer seal of an embodiment of the present invention at panels A-C.

FIG. 10 at panels A-C illustrates cross sectional views of the large version of the inner seal 1001A, middle seal 1001B, and outer seal 1001C, which position the present invention onto the ear canal of the user.

What is claimed is:

1. A sound attenuating device for attenuating sound entering an ear of a subject, the device comprising:
   a. a flat concha tab adapted for insertion into the concha cavum of the ear of the subject, and for gripping by the subject for removal of the entire device from the ear canal of the subject, wherein at least a portion of the concha tab is adapted to tuck under the antitragus of the ear of the subject when inserted, the flat concha tab including:
      i. a distal end adapted to be spaced away from the ear canal of the subject and which curves away from the ear of the subject,
      ii. a proximal end,
      iii. a first surface adapted to face the ear of the subject,
      iv. a second surface adapted to face away from the ear of the subject the second surface being opposite the first surface, and
      v. a sound inlet arranged on the second surface, adjacent to the distal end of the concha tab;
   b. a sound bore, wherein the sound bore:
      i. is adapted for positioning within and along at least a portion of the concha tab, and ii. a portion of the sound bore being parallel to at least one of the first surface and the second surface, and includes a first end in communication with the sound inlet, and a second end;
 c. a hollow tube including:
  i. a proximal end attached to the first surface and in communication with the second end of the sound bore, and
  ii. a distal end adapted to protrude into the ear canal of the subject when the device is inserted in the ear of the subject; and
 d. at least one seal attached to and encapsulating another portion of the sound bore.

2. The device of claim 1, wherein the device further comprises a sound attenuating filter arranged within at least one of the hollow tube and the sound bore.

3. The device of claim 1, wherein the hollow tube is connected to the first surface at an angle of at least 45 degrees.

4. The device of claim 1, wherein the hollow tube is connected to the first surface at an angle that is within 25 degrees of perpendicularity to the first face.

\* \* \* \* \*